United States Patent [19]

Sinclair et al.

[11] 4,019,865
[45] Apr. 26, 1977

[54] H₂S INDICATOR

[75] Inventors: Robin A. Sinclair, St. Paul, Minn.; Eileen A. Glasspoole, Hudson, Wis.

[73] Assignee: Minnesota Mining and Manufacturing Company, St. Paul, Minn.

[22] Filed: Feb. 13, 1976

[21] Appl. No.: 658,127

[52] U.S. Cl. .................. 23/253 TP; 23/254 R; 116/114 AM

[51] Int. Cl.² .................. G01N 21/12; G01N 31/22

[58] Field of Search .......... 23/232 R, 253 TP, 254; 116/114 AM

[56] References Cited

UNITED STATES PATENTS

| | | | |
|---|---|---|---|
| 3,223,487 | 12/1965 | Grosskopf | 23/254 R |
| 3,715,192 | 2/1973 | Wenz | 23/253 TP |

OTHER PUBLICATIONS

Chemical Abstracts, 66:34627n (1967).

*Primary Examiner*—Morris O. Wolk
*Assistant Examiner*—Sidney Marantz
*Attorney, Agent, or Firm*—Cruzan Alexander; Donald M. Sell; Mark A. Litman

[57] ABSTRACT

The prolonged attainment of high concentrations of H₂S in a gaseous environment is indicated by a device which comprises a base, an enclosing upper surface which is transparent and water impenetrable, and a light stable composition enclosed by the base and upper surface, said composition undergoing a visible change in color or tone when exposed to a constant concentration of 1 part per million of H₂S for one day.

10 Claims, No Drawings

H₂S INDICATOR

The attainment and preservation of noble metals has been an objective of mankind since time immemorial. A branch of quasi-science, alchemy, was even devoted to seeking methods of synthesizing gold. These noble metals, particularly platinum, gold, and silver have been valued for their aesthetic merits. Silver suffers from a problem unique to these aesthetic noble metals in that it readlily tarnishes while the others are essentially inert to environmental deterioration.

For many years, antitarnish compositions and devices have been used to prevent tarnish of silver, particularly by absorbing corrosive materials. Such devices are represented by U.S. Pat. Nos. 1,561,650; 1,628,610; 1,985,900; 2,151,053; 2,323,369; 2,503,843; 2,531,114; and 2,749,210. These and other tarnish preventatives have had various levels of success.

One particular problem has existed with these devices since their original use, but has heretofore never been overcome. Most of the antitarnish products work by reaction or absorption of the corrosive material (particularly $H_2S$) from the air. However, these products all have a finite limit of utility, when the material becomes nearly completed reacted, the absorption sites are nearly filled. To date, the only way in recognizing that the antitarnish device is no longer operating is to notice that the silver is tarnished, which is, of course, completely contradictory to the purpose of the antitarnish device.

It is one aspect of the present invention to provide an indicator which can itself indicate the diminishing utility of antitarnish devices prior to the tarnishing of the silver to be protected.

In its broadest aspect, the present invention relates to a device for indicating the prolonged (i.e., not instantaneous, momentary, or transient) attainment within a gaseous environment of a concentration of $H_2S$ sufficient to tarnish free metal silver in said environment before tarnishing of said free metal silver comprising a base support surface, an upper surface forming at least an enclosed volume (i.e., a volume sufficient to physically retain and enclose the hereinafter described active ingredient therein) with said support surface, said upper surface having a translucent or transparent portion exposing at least a part of said enclosing volume, and a composition within said volume which undergoes a visible change or intensification in tone or color when reacted with $H_2S$, said composition undergoing said visible change or intensification when exposed to a constant atmospheric concentration of 1 part per million of $H_2S$.

The viewing portion of the upper surface (the transparent or translucent portion exposing the volume) should be arranged so as to expose that portion of the indicating composition which is most readily exposed to the environmental $H_2S$. For example, if the upper surface is in the shape of a disc, with side vents for admission of the gas, the viewing portion must extend to the extreme sides of the enclosed composition where the visible change will first occur. It is preferred to have the viewing portion penetrable by $H_2S$ so that the composition in contact with the viewing portion is also that first contacted by entering vapors. It is more preferred, when the indicating composition is in liquid or liquid solution form, that the penetrability of the system to $H_2S$ exceed the penetrability by the liquid material. Selection of pore size would readily effect this.

Certain parameters are desirable if not critical to the practice of the present invention and will hereinafter be described.

The visible change which occurs in the composition must be readily visible to serve a useful purpose. In general, when the change is only an intensification of color or tone, the change must be at least 0.2 in optical density and preferably at least 0.4. When the change is from one color to another or white to a color, the change need not be so critically defined as long as the colors are visible.

It is essential that the indicating composition undergo this visible change within 1 day when exposed to a constant concentration of 1 part per million (1 ppm) of $H_2S$. Preferably the change will occur within 1 day when exposed to a constant concentration of at most 50 parts per billion (ppb) of $H_2S$ and most preferably 2 ppb of $H_2S$.

The indicating device of the present invention is most useful when combined with an antitarnish absorbent for $H_2S$. These devices must have a static equilibrium vapor pressure with $H_2S$ which is at most one-tenth the constant concentration level of $H_2S$ at which the composition will undergo said visible change within one day and preferably no more than one-hundredth of that concentration level.

In the selection of indicating compositions, solutions of metal salts are more reactive than solids or suspensions, although the solids and suspensions of such salts are useful if they meet the functional requirements of the present invention. Silver nitrate, lead acetate and mercuric nitrate are examples of indicator materials. Nitrate is a preferred anion on all metal salt indicators because of the fact that such metal salts are more reactive when combined with nitrate than with other anions. Glycerol provides a good solvent or medium for the salts as it is not volatile and is generally non-reactive with environmental corrosives.

The indicating composition and its sulfide product must be light-stable. That is, the composition must not undergo a visible change in color or tone because of exposure to conventional fluorescent room lighting for a period of at least 30 days and its sulfide product must not be photolabile under the same conditions.

The transparent or translucent viewing portion ought not be water-penetrable. That is, the surface will not pass water through it if lightly swabbed with moist (but not dripping) cotton.

The silver, lead and mercury nitrates are colorless and convert to dark-colored brown-black sulfides, providing a good visible change. Bismuth nitrate and bismuth subnitrate ($BiONO_3$) also go from colorless materials to brown-black sulfides. Copper sulfate is water soluble and goes from blue to near black. Ferric sulfate goes from red-brown to dark brown. Generally any transition metal salt (except sulfides, of course) are useful. Solutions in polyhydric alcohols are good media for use in the present invention.

EXAMPLE 1

$Bi(NO_3)_3 \cdot 5H_2O$ was dissolved in 50 percent by weight $HNO_3$ (10 ml) and mixed with porous ceramic beads as a support. This mixture was placed in a tube and heated under $N_2$ to 300° C at a heating rate of 10° C/min. After 1 hour at 300° C the mixture was cooled and placed on a solid substrate with a porous top surface. This showed a significant color change (white to tan) in less than 1 hour at an $H_2S$ concentration of 1 ppm.

EXAMPLE 2

Example 1 was repeated except that a polymethymethacrylate binder was added to the particles and the mixture pressed into coherent form at 4500 Kg pressure at 149° C. The pressed indicator disc was placed on a white background surface for greater constrast. The yellow bismuth sulfide stain again readily appeared within an hour of constant exposure to 1 ppm $H_2S$.

EXAMPLE 3

A 10% by weight solution of bismuth subnitrate in glycerol was absorbed by Whatman No. 1 filter paper. 5mm diameter discs were cut out and adhesively secured to a 0.5mm thick polypropylene microfiber sheet and covered with 3M Micropore transparent tape, which contains numerous pores which are vapor transmissive but not water penetrable.

The discs were placed in a 1770cc polycarbonate box and $H_2S$ injected. The results are tabulated below.

| Initial $H_2S$ Concentration ppb | $H_2S$ micrograms | Time to discoloration (min) |
| --- | --- | --- |
| 1000 | 2.5 | 30 |
| 500 | 1.25 | 45 |
| 250 | 0.63 | 90 |
| 100 | 0.25 | 105 |
| 50 | 0.13 | 120 |

We claim:
1. A device for indicating the prolonged attainment within a gaseous environment of a concentration of $H_2S$ sufficient to tarnish free metal silver in said environment before tarnishing of said free metal silver comprising:
 1. a base support surface,
 2. an upper surface which is not water penetrable forming at least an enclosed volume with said support surface, said upper surface having a translucent or transparent portion exposing at least a part of said enclosed volume and allowing penetration of vapor through said upper surface so that penetrating vapor will contact:
 3. a light-stable composition within said enclosed volume which undergoes a visible light-stable change which is a change in tone or color or intensification of its tone or color when reacted with $H_2S$, said composition undergoing said visible change within 1 day when exposed to a constant concentration of 1 part per million of $H_2S$, and said composition in said enclosed volume having free vapor access to its surrounding environment.

2. The device of claim 1 wherein the visible change is from colorless to colored or from white to a color or tone having an optical density of at least 0.2.

3. The device of claim 1 wherein said composition will undergo said visible change within 1 day when exposed to a constant concentration of less than 50 parts per billion of $H_2S$.

4. The device of claim 1 wherein said composition will undergo said visible change within 1 day when exposed to a constant concentration of less than 2 parts per billion of $H_2S$.

5. The device of claim 1 in combination with an absorbent for $H_2S$ which has a static equilibrium vapor pressure with $H_2S$ which is at most one-tenth the constant concentration level of $H_2S$ at which the composition will undergo said visible change within 1 day.

6. The device of claim 1 in combination with an absorbent for $H_2S$ which has a static equilibrium vapor pressure with $H_2S$ which is at most one-hundredth constant concentration level of $H_2S$ at which the composition will undergo said visible change within 1 day.

7. The device of claim 1 wherein the composition within said volume is a solution of a transition metal salt other than a sulfide.

8. The device of claim 7 wherein the solvent of said solution is a polyhydric alcohol.

9. The device of claim 7 wherein the salt is a transition metal nitrate.

10. The device of claim 9 wherein the solvent of said solution is a polyhydric alcohol.

* * * * *